(12) United States Patent
Blot et al.

(10) Patent No.: US 11,680,912 B2
(45) Date of Patent: Jun. 20, 2023

(54) SENSOR SYSTEM TO APPLY ELECTROMAGNETIC FIELDS FOR ELECTROMAGNETIC IMPEDANCE SPECTROSCOPY IN-PROCESS MONITORING OF FLUIDS

(71) Applicant: TransTech Systems, Inc., Latham, NY (US)

(72) Inventors: Adam D. Blot, Altamont, NY (US); Manfred Geier, Oakland, CA (US); Andrew J. Westcott, Troy, NY (US)

(73) Assignee: TRANSTECH SYSTEMS, INC., Latham, NY (US)

( * ) Notice: Subject to any disclaimer, the term of this patent is extended or adjusted under 35 U.S.C. 154(b) by 71 days.

(21) Appl. No.: 17/320,586

(22) Filed: May 14, 2021

(65) Prior Publication Data
US 2021/0356409 A1 Nov. 18, 2021

Related U.S. Application Data

(60) Provisional application No. 63/024,765, filed on May 14, 2020.

(51) Int. Cl.
*G01R 27/04* (2006.01)
*G01R 27/32* (2006.01)
(Continued)

(52) U.S. Cl.
CPC ......... *G01N 22/00* (2013.01); *G01N 21/3581* (2013.01); *G01N 22/04* (2013.01);
(Continued)

(58) Field of Classification Search
CPC ........ G01N 22/00; G01N 33/03; G01N 33/04; G01N 27/026; G01N 22/04; G01N 21/3581; G01R 27/28; G01R 27/04; G01R 27/06
(Continued)

(56) References Cited

U.S. PATENT DOCUMENTS 7,219,024 B2 5/2007 Gamache et al.
9,372,183 B2 6/2016 Di Berardino et al.
(Continued)

FOREIGN PATENT DOCUMENTS

WO 2020/236859 A1 11/2020

*Primary Examiner* — Raul J Rios Russo
(74) *Attorney, Agent, or Firm* — Hoffman Warnick LLC

(57) ABSTRACT

Various implementations include systems and approaches for measuring an electromagnetic impedance characteristic of a fluid under test (FUT) in a fluid channel. In some cases, a system includes: a transmitting electrode assembly including: a transmitting electrode having a transmitting surface; and a transmitting electrode backer ground plate at least partially surrounding the transmitting electrode; a receiving electrode assembly including: a receiving electrode having a receiving surface; and a receiving electrode backer ground plate at least partially surrounding the receiving electrode, where the transmitting electrode and the receiving electrode are located in a set of walls defining the fluid channel, the transmitting surface and the receiving surface each conform to a shape of the set of walls defining the fluid channel, where the fluid channel permits transverse flow of the FUT relative to both the transmitting electrode and the receiving electrode.

20 Claims, 12 Drawing Sheets

(51) Int. Cl.
*G01N 22/00* (2006.01)
*G01N 22/04* (2006.01)
*G01N 21/3581* (2014.01)
*G01R 27/28* (2006.01)
*G01R 27/06* (2006.01)

(52) U.S. Cl.
CPC .............. *G01R 27/04* (2013.01); *G01R 27/06* (2013.01); *G01R 27/28* (2013.01)

(58) Field of Classification Search
USPC ... 324/76.11–76.83, 459, 600, 629, 637, 639
See application file for complete search history.

(56) References Cited

U.S. PATENT DOCUMENTS

| | | |
|---|---|---|
| 9,389,175 B2 | 7/2016 | Deshpande et al. |
| 9,465,061 B2 | 10/2016 | Colosimo et al. |
| 9,494,538 B2 | 11/2016 | Kozicki et al. |
| 9,797,855 B2 | 10/2017 | Heidmann et al. |
| 2010/0164513 A1* | 7/2010 | Rapoport ............... G01N 22/00 324/633 |
| 2013/0049770 A1 | 2/2013 | Basu et al. |
| 2015/0137831 A1* | 5/2015 | Pluta ................... A61B 5/0536 324/647 |
| 2016/0054247 A1* | 2/2016 | Colosimo ............ G01N 27/026 324/629 |
| 2020/0011811 A1* | 1/2020 | Macdonald ........ A61B 5/14532 |
| 2021/0055280 A1 | 2/2021 | Geier et al. |
| 2021/0285905 A1* | 9/2021 | Hillebrand ............. G01N 33/18 |

\* cited by examiner

SENSOR SYSTEM TO APPLY ELECTROMAGNETIC FIELDS FOR ELECTROMAGNETIC IMPEDANCE SPECTROSCOPY IN-PROCESS MONITORING OF FLUIDS

PRIORITY CLAIM

This application claims priority to U.S. Provisional Patent Application No. 63/024,765, filed on May 14, 2020, which is herein incorporated by reference in its entirety.

TECHNICAL FIELD

This disclosure relates generally to characterizing physical properties of a fluid during a manufacturing process by applying electromagnetic impedance spectroscopy. In particular, this disclosure presents a sensor system that applies electromagnetic fields to the fluid as it flows through a piping or a flow channel system for in-process characterization of some physical attribute(s) of the fluid.

BACKGROUND

There is a need for a sensor system which can be used in line with the processing of fluids including, e.g., dairy, food oils, and industrial fluids. Conventional systems fail to effectively characterize such fluids in-process.

SUMMARY

In U.S. Pat. No. 7,219,024 (hereby incorporated by reference in its entirety), a system is described for conducting electromagnetic impedance spectroscopy (EIS) to non-invasively determine the in-place compaction (i.e., density) and moisture of various engineering materials, with specific interest in soils. This system uses a manually operated gauge to conduct the testing. U.S. Pat. No. 9,465,061 (hereby incorporated by reference in its entirety) describes a method of conducting an in-process inspection of solid materials with EIS. There is a need to conduct in-process inspections and characterizations of fluids as suggested by U.S. Pat. Nos. 9,372,183, 9,389,175, and 9,797,855 (each hereby incorporated by reference in its entirety). The fluid of interest in these patents is milk. While the sensor system of the present disclosure can be applied to any fluid, including a gas, the description will primarily address its application to milk. U.S. Pat. No. 9,389,175 applies an optical detections system and U.S. Pat. Nos. 9,372,183 and 9,797,855 apply impedance flow cytometry, which counts and characterizes cells. The references cited in this application discuss various electromagnetic methods of characterizing dairy products (milk) and other foods such as olive oil (Reference 2), along with fruits, vegetable oils, cookies, pork, and fish (Reference 6). All of the referenced methods use a sensor system that is designed for laboratory use or focus on the analysis algorithm. As noted herein, there is a need for a sensor system which can be used in line with the processing of fluids including dairy, food oils, and industrial fluids. Reference 4 suggests that an in-process method of evaluating dairy products may aid a processor to comply with International Standards Organization (ISO) Standard 22000:18, Food Safety Management Systems—Requirements for any Organization in the Food Chain. U.S. patent application Ser. No. 16/640,157 (hereby incorporated by reference in its entirety) describes a parallel plate test assembly for use in characterizing the electromagnetic properties of a material under test with specific interest in soils in a laboratory setting. U.S. patent application Ser. No. 62/851,319 (hereby incorporated by reference in its entirety) describes a sensor system that generates parallel electromagnetic field lines in a specified measurement volume for use in characterizing the electromagnetic properties of a material under test with specific interest in fluids in an industrial process.

All examples and features mentioned below can be combined in any technically possible way.

Various aspects of this disclosure relate to sensor systems in which the electromagnetic field lines in the measurement volume of the fluid under test (FUT) are not parallel, but instead have a complex three dimensional pattern. Additionally, the measurement volume is defined by the electromagnetic field lines which are determined by the electrode geometry (e.g., size), the flow channel geometry (e.g., diameter), and the test fluid electromagnetic characteristics. In some cases, these sensor systems are described as "non-parallel sensor systems" and certain approaches comprise the installation of the non-parallel sensor systems into a flow channel enclosing a fluid, liquid or gas, which is being monitored as part of a production or other process. The non-parallel sensor systems, which are inserted in the process flow, are comprised of either a non-parallel sensor system of circular transmitting and receiving electrodes diametrically opposed across the flow channel with the electromagnetic field perpendicular to the flow or a non-parallel sensor system of a cylindrical transmitting and receiving electrodes positioned in line with the flow channel with the electromagnetic field parallel to the flow. In various implementations, these electrodes conform to the wall geometry of the flow channel. These electrodes are connected to the transmitting and receiving terminals of signal generator/analyzer. The electrodes have a conducting backer ground plates which form volumes by at least partially surrounding the electrodes and proximate to the electrodes. The conducting backer ground plates for the receiving electrodes may at least partially surround the electrode and extend in the plane of the receiving electrode to provide for a guard ring for the receiving electrode. The conducting backer ground plates of the electrodes are connected to the system ground of the signal generating means. The electromagnetic field is generated at a single frequency within a range of selected frequencies or over a range of selected frequencies by signal generator and analyzer means known in the art. Development of an algorithm to correlate specified physical parameters of the FUT to the measured impedance or dielectric spectrographic features is accomplished by application of methods known in the art such as analysis of variance (ANOVA), neural nets, and deep learning.

Various aspects of the disclosure provide methods for the in-process characterization of fluids through sensor systems that provides for EIS. The sensor systems comprise transmitting and receiving electrode assemblies. The sensor systems provide for the generation of electromagnetic field lines perpendicular and parallel to the flow of the FUT. The electromagnetic signals are generated over a range of frequencies specific to the FUT. In various implementations, the frequencies selected fall within the range of approximately 1 KHz to 100 MHz, with a particularly beneficial sub-range being approximately 100 KHz to 20 MHz. The resultant measured impedance or dielectric spectrum over a selected range of frequencies is correlated with a specific physical characteristic(s) of the FUT. These correlations can be used to create algorithms that relate a specific impedance-frequency pattern with the specified physical characteristic(s).

The sensor systems disclosed according to various implementations enable the generation of an electromagnetic field with a fixed measurement volume defined by volume of the electromagnetic field within the flow channel. The volume of the electromagnetic field is defined by the sensor geometry and the electromagnetic characteristics of the FUT. For a specific sensor geometry and FUT, the electromagnetic field volume and measurement volume are consistent.

The sensor systems disclosed according to various implementations may be comprised of a single sensor system (e.g., corresponding single transmitting electrode and receiving electrode), through which the entire range of frequencies are transmitted. Alternately, multiple sensors may be used, each transmitting a single frequency or subsets of the total range of frequencies desired for characterizing the specific FUT.

Some embodiments of the sensor system are comprised of a circular or rectangular transmitting electrode and an equivalently sized and shaped receiving electrode located on opposite sides of the flow channel for the FUT and conforming to wall geometry of the flow channel. In these embodiments, the electromagnetic field in nominally perpendicular to the flow of the FUT. The transmitting electrode has a conductive ground backer plate which acts as the back plane of the electrode and at least partially surrounds the volume proximate to the transmitting electrode. The receiving electrode also has a conductive ground backer plate and at least partially surrounds the volume proximate to the receiving electrode. The conductive ground backer plates may each extend from the front plane of the electrodes and may include a section that is coplanar with each corresponding electrode.

An additional embodiment of the sensor system includes both a transmitting and a receiving electrode sequentially located longitudinally along the flow channel and conforming to the wall geometry of the flow channel. A conductive ground backer plate at least partially surrounds both electrodes with separate volumes between the backer plate and proximate to each of the electrodes. The conductive ground backer plate extends from the front plane of the electrodes and may include a section that is coplanar with the electrodes and surrounds the electrodes. In particular cases, the electrodes transverse the interior circumference of the flow channel (e.g., where the flow channel has a cylindrical geometry), with the electrodes located sequentially along the longitudinal axes of the flow channel. In this embodiment, the electromagnetic field in nominally parallel to the flow of the FUT.

In another embodiment, the sensor system includes multiple sets of two separate rectangular sensors that are equally sized and are located on diametrically opposite sides of the flow channel relative to the FUT. In these cases, separate sets of the rectangular transmitting and receiving sensors are placed along the flow channel in the same radial positions. In this embodiment, the transmitting and receiving electrodes of one sensor system are aligned with the transmitting and receiving electrodes of the other(s). In some embodiments, the electrodes subsume an arc on the interior circumference of a cylindrical flow channel.

In particular embodiments, the sensor systems are shaped to match the geometry of the flow channel for the FUT. In certain cases, the flow channel is substantially cylindrical in shape, e.g., including a cylindrical pipe in some embodiments.

In certain implementations, the walls of the flow channel in the region proximate the sensors are constructed of non-conducting material. In other implementations, the walls of the container are constructed of a conducting material but include a non-conducting liner such that the FUT is not in electrical contact with the walls of the container. In these cases, the non-conducting surface extends upstream and downstream of the sensors by a distance, e.g., at least twice the largest dimension of the sensor length (along the fluid flow axis). This distance can extend from the upstream and downstream edges of the backer ground plate and include the region of the sensor systems in the flow channel. Additionally, in various implementations the conductive ground backer plates are electrically isolated from both the flow channel of the flow of the FUT and from the electrodes. The sensor electrodes may either be in electrically conductive contact with the FUT or in non-conducting contact. In certain implementations, the walls of the interior of the flow channel and the sensor surfaces form a smooth surface without any perturbations or gaps.

The transmitting and receiving sensor electrodes may be connected to transmitting and receiving connections of a specifically designed signal generating and analyzing circuit as shown in U.S. patent application Ser. No. 16/640,157 and in FIG. 7 herein. The signal generating and analyzing functions may also be provided by methods known in the art, e.g., an LCR Meter such as the Keysight E4980A LCR/Impedance Analyzer or an impedance analyzer such as the Keysight E9990A Impedance Analyzer. In all cases, the conductive ground backer plate of the transmitting and receiving electrode are connected to the system ground.

In certain cases, the transmitting and receiving sensor electrodes are in conducting electrical contact with the FUT.

In certain cases, the transmitting and receiving sensor electrodes are in non-conducting electrical contact with the FUT.

In certain cases, the electrically non-conducting container or liner includes plastics such as polyethylene, polyvinyl chloride (PVC), polytetrafluoroethylene (Teflon), poly carbonate, and/or various fiber glass reinforce epoxy laminate materials (e.g. FR-4). In some cases, the electrically non-conducting container is formed of a poly methyl methacrylate (PMMA or acrylic), which is substantially transparent and allows for visual observation of the testing process.

As noted herein, the FUT may be an inorganic fluid, an organic fluid (e.g. milk, olive oil, etc.), or a biological fluid (e.g. blood). In addition to liquids, the FUT may also be gaseous.

Unlike the electromagnetic field pattern in U.S. patent application Ser. No. 62/851,319, the electromagnetic fields from the sensor systems described here do not necessarily generate parallel field lines with a well-defined measurement volume. In various implementations, the electrodes of the sensor systems described here are curvilinear and generate a complex three-dimensional field pattern. Accordingly, generation of algorithms correlating the measured impedance spectroscopy to physical properties of the FUT may require advanced mathematical methods such as ANOVA, neural networks and deep learning techniques.

Particular implementations include systems and approaches for measuring an electromagnetic impedance characteristic of a FUT in a fluid channel. In some cases, a system includes: a transmitting electrode assembly including: a transmitting electrode having a transmitting surface; and a transmitting electrode backer ground plate at least partially surrounding the transmitting electrode; a receiving electrode assembly including: a receiving electrode having a receiving surface; and a receiving electrode backer ground plate at least partially surrounding the receiving electrode, where the transmitting electrode and the receiving electrode are located in a set of walls defining the fluid channel, the transmitting surface and the receiving surface each conform to a shape of the set of walls defining the fluid channel, wherein the fluid channel permits transverse flow of the FUT relative to both the transmitting electrode and the receiving electrode.

Additional implementations include a method of measuring an electromagnetic impedance characteristic of a fluid under test (FUT) in a fluid channel. In certain cases, the method includes: providing a system having: a transmitting electrode assembly comprising: a transmitting electrode having a transmitting surface; and a transmitting electrode backer ground plate at least partially surrounding the transmitting electrode; a receiving electrode assembly comprising: a receiving electrode having receiving surface; and a receiving electrode backer ground plate at least partially surrounding the receiving electrode, wherein the transmitting electrode and the receiving electrode are located in a set of walls defining the fluid channel, the transmitting surface and the receiving surface each conform to a shape of the set of walls defining the fluid channel; flowing the FUT through the fluid channel; transmitting a set of electromagnetic signals from the transmitting electrode, through the FUT, to the receiving electrode while flowing the FUT through the fluid channel; and detecting a change in the set of electromagnetic signals from the transmitting electrode to the receiving electrode.

In certain cases, the transmitting electrode is substantially parallel with the receiving electrode, and a center of the transmitting electrode is aligned with a center of the receiving electrode.

In particular aspects, the transmitting electrode backer ground plate is electrically grounded and insulated from the transmitting electrode, and wherein the transmitting electrode backer ground plate extends from a plane formed by the transmitting electrode and creates an electrically isolated volume proximate the transmitting electrode; wherein the receiving electrode backer ground plate is electrically grounded and insulated from the receiving electrode, and wherein the receiving electrode backer ground plate extends from a plane formed by the receiving electrode and creates an electrically isolated volume proximate the receiving electrode; and wherein the receiving electrode backer ground plate may extend into the plane of the receiving electrode and be coplanar with the receiving electrode.

In some implementations, the transmitting electrode backer ground plate has a surface that is coplanar with the transmitting electrode in the fluid channel, and wherein the receiving electrode backer ground plate has a surface that is coplanar with the receiving electrode in the fluid channel.

In certain cases, the backer ground plates extend into the plane of the corresponding electrode and are coplanar with the corresponding electrode.

In particular aspects, the transmitting electrode conductive backer ground plate and the receiving electrode conductive backer ground plate are each circular, and wherein a diameter of the transmitting electrode is equal to approximately a diameter of the receiving electrode. In some implementations, the transmitting and receiving electrodes have the same shape as the corresponding conductive backer ground plates.

In certain cases, the set of walls includes a pair of openings including an inlet and an outlet, wherein the FUT flows from the inlet to the outlet, and wherein the transmitting electrode assembly and the receiving electrode assembly are located between the openings.

In some implementations, the transmitting electrode and the receiving electrode have a rectangular shape, an oval shape, or an elliptical shape.

In particular cases, the transmitting electrode and the receiving electrode are defined by rings with a cylindrical geometry conforming to the inner surface of the set of walls of the fluid flow channel.

In some cases, the transmitting electrode conductive backer ground plate and the receiving electrode conductive backer ground plate are integral with the set of walls defining the fluid channel.

In particular implementations, the transmitting electrode and the receiving electrode are axially adjacent one another in the fluid channel.

In certain aspects, the transmitting electrode is located upstream of the receiving electrode or the receiving electrode is located upstream of the transmitting electrode.

In particular cases, the FUT comprises a liquid or a gas.

In some implementations, the FUT comprises an organic fluid.

In certain cases, the organic fluid comprises milk.

In some aspects, the transmitting electrode and the receiving electrode are in electrically conducting contact with the FUT.

In particular implementations, the transmitting electrode and the receiving electrode are in non-electrical conducting contact with the FUT.

In some cases, the transmitting electrode assembly comprises at least one additional transmitting electrode and wherein the receiving electrode assembly comprises at least one additional receiving electrode, wherein respective electrodes in the transmitting electrode assembly are configured to operate at a single frequency or at distinct frequencies within a range of selected frequencies, and wherein respective electrodes in the receiving electrode assembly are configured to operate at the single frequency or at the distinct frequencies within the range of selected frequencies.

In certain cases, adjacent electrodes in each of the transmitting electrode assembly and the receiving electrode assembly have a same function such that two transmitting electrodes are located adjacent one another on one side of the fluid channel and two receiving electrodes are located adjacent one another on the opposite side of the fluid channel.

In particular aspects, the system further includes a signal generator/analyzer coupled with the transmitting electrode and the receiving electrode, the signal generator/analyzer comprising: a generator component configured to initiate transmission of a set of electromagnetic signals from the transmitting electrode, through the FUT, to the receiving electrode; and an analyzer component configured to detect a change in the set of electromagnetic signals from the transmitting electrode to the receiving electrode.

In some cases, the set of electromagnetic signals are transmitted over a frequency range of approximately 1 kilo-Hertz to approximately 100 mega-Hertz.

In certain aspects, the system further includes a computing device coupled with the signal generator/analyzer, wherein the computing device is configured to determine a characteristic of the FUT based upon a change in the set of electromagnetic signals from the transmitting electrode to the receiving electrode.

In particular implementations, determining the characteristic of the FUT comprises: determining a difference in an aspect of the set of electromagnetic signals; comparing the difference in the aspect to a predetermined threshold; and determining a characteristic of the FUT based on the compared difference.

In some implementations, determining the characteristic of the FUT comprises: computing impedance or dielectric characteristics of the FUT; and applying an established correlation algorithm to the computed impedance or dielectric characteristics to determine the characteristic of the FUT.

In certain cases, the set of electromagnetic signals define an electromagnetic field including field lines extending between the transmitting electrode and the receiving electrode, and wherein a size of the electromagnetic field is fixed based upon the geometry of the sensor system (e.g., size of electrodes), a diameter of the fluid channel, and electromagnetic properties of the FUT.

In particular aspects, the transmitting electrode backer ground plate extends from a plane formed by the transmitting electrode and creates an electrically isolated volume proximate the transmitting electrode, and wherein the receiving electrode backer ground plate extends from a plane formed by the receiving electrode and creates an electrically isolated volume proximate the receiving electrode, wherein each electrically isolated volume is defined by a distance ($d_T$ and $d_R$) between a back of the transmitting electrode and the transmitting backer ground plate, and a back of the receiving electrode and the receiving backer ground plate, respectively.

In some cases, during use, parasitic capacitances in the electrically isolated volumes are at least partially controlled by the selected distances ($d_T$ and $d_R$).

Two or more features described in this disclosure, including those described in this summary section, may be combined to form implementations not specifically described herein The details of one or more implementations are set forth in the accompanying drawings and the description below. Other features, objects and advantages will be apparent from the description and drawings, and from the claims.

BRIEF DESCRIPTION OF THE DRAWINGS

The embodiments of this disclosure will be described in detail, with reference to the following figures, wherein like designations denote like elements, and wherein.

Figure 1:
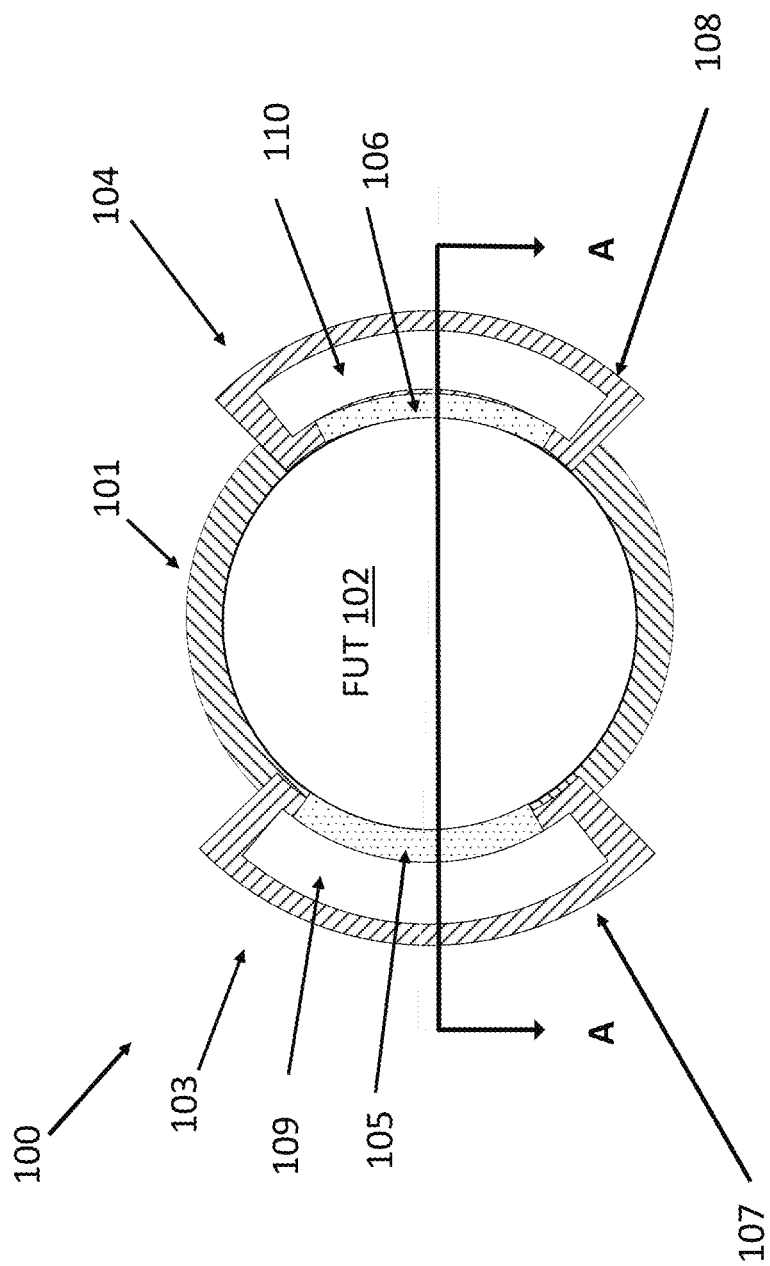
FIG. 1 is an end sectional view of a fluid channel with components in a sensor according to various implementations.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

As noted herein, this disclosure relates to sensor systems to characterize physical attribute(s) of a fluid by transmitting a complex pattern of three-dimensional electromagnetic field lines at a frequency (e.g., specific frequency or over a range of frequencies) through the fluid as it flows within a channel (or, conduit). The electromagnetic field may be generated by various known approaches, described for example in the US Patent Applications incorporated by reference herein. There are many methods for correlating the measured impedance or dielectric at varying frequencies to physical attribute(s) of the fluid under test (FUT), as described in the US Patent Applications incorporated by reference herein and known in the art, including for example, analysis of variance (ANOVA) and various forms of neural networks including deep learning methods.

FIG. 1 presents an end cross sectional view of a sensor system 100 looking down a fluid channel 101, according to various implementations. In this view, the FUT 102 is shown in the fluid channel 101. Two sensor system electrode assemblies 103 and 104 are show on either side of the fluid channel 101. Each electrode assembly 103, 104 includes an electrode 105 and 106, respectively, and a conducting backer ground plate 107 and 108, respectively. The conducting backer ground plates 107, 108 encloses (capacitive) volumes 109 and 110, respectively, behind the electrodes 105, 106. That is, the conducting backer ground plates (or simply, plates) 107, 108 define the capacitive volumes 109, 110 behind the electrodes 105, 106. In various implementations, the plates 107, 108 at least partially surround the electrodes 105, 106. In this view and FIGS. 2A and 2B, electrode 105 is the transmitting electrode and electrode 106 is the receiving electrode. In some cases, the electrodes 105, 106 are diametrically opposed with respect each other across the fluid channel 101, and in some cases, the electrodes 105, 106 have similar (or nearly identical) sizes and are in alignment with each other such the centers of their transmitting surfaces are directly opposite each other across the fluid channel 101. The designation of receiving or transmitting electrode is further described herein.

Figure 2A:
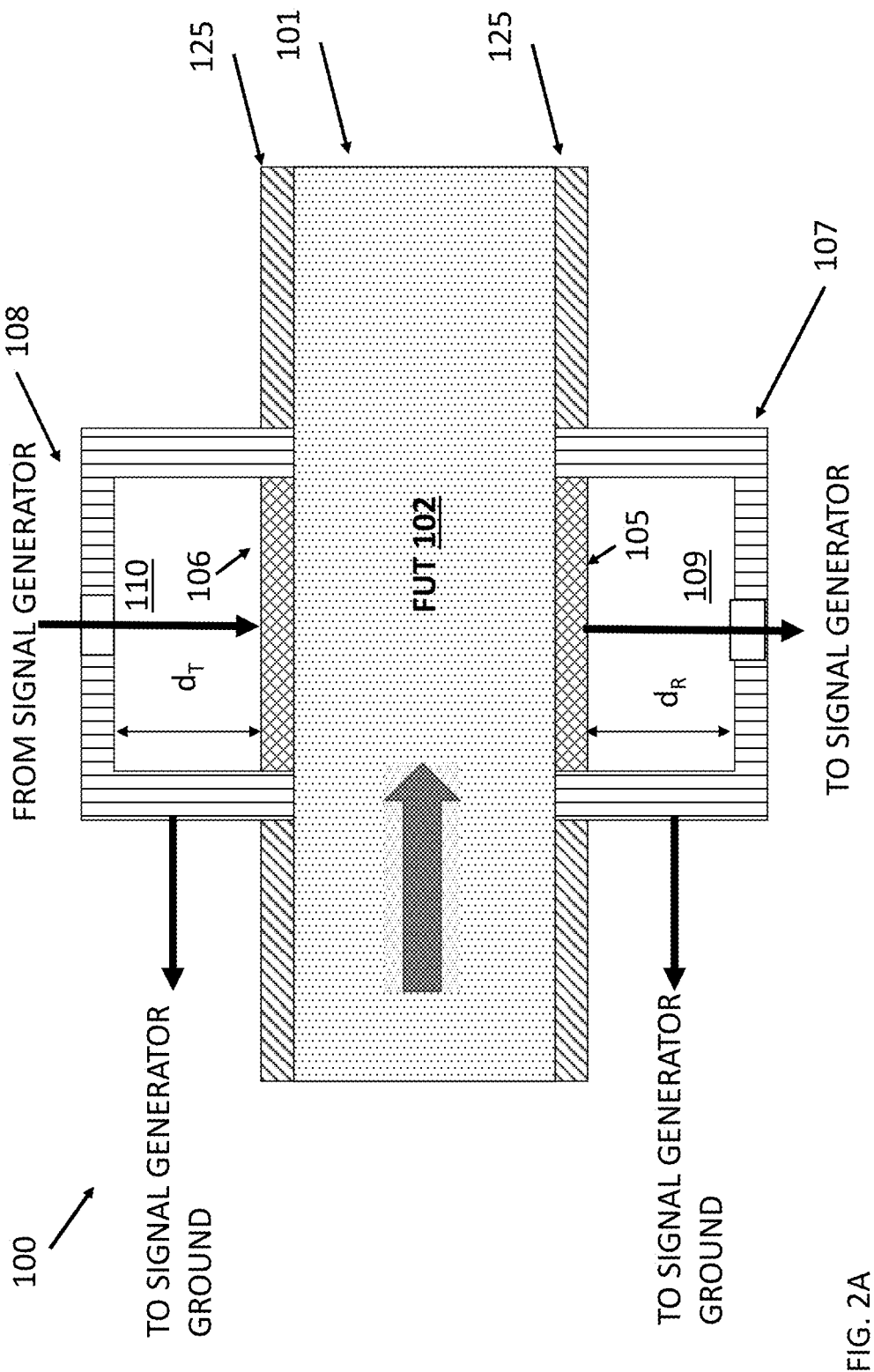
FIG. 2A is a sectional view of the sensor system in FIG. 1 according to various implementations.
Figure 2B:
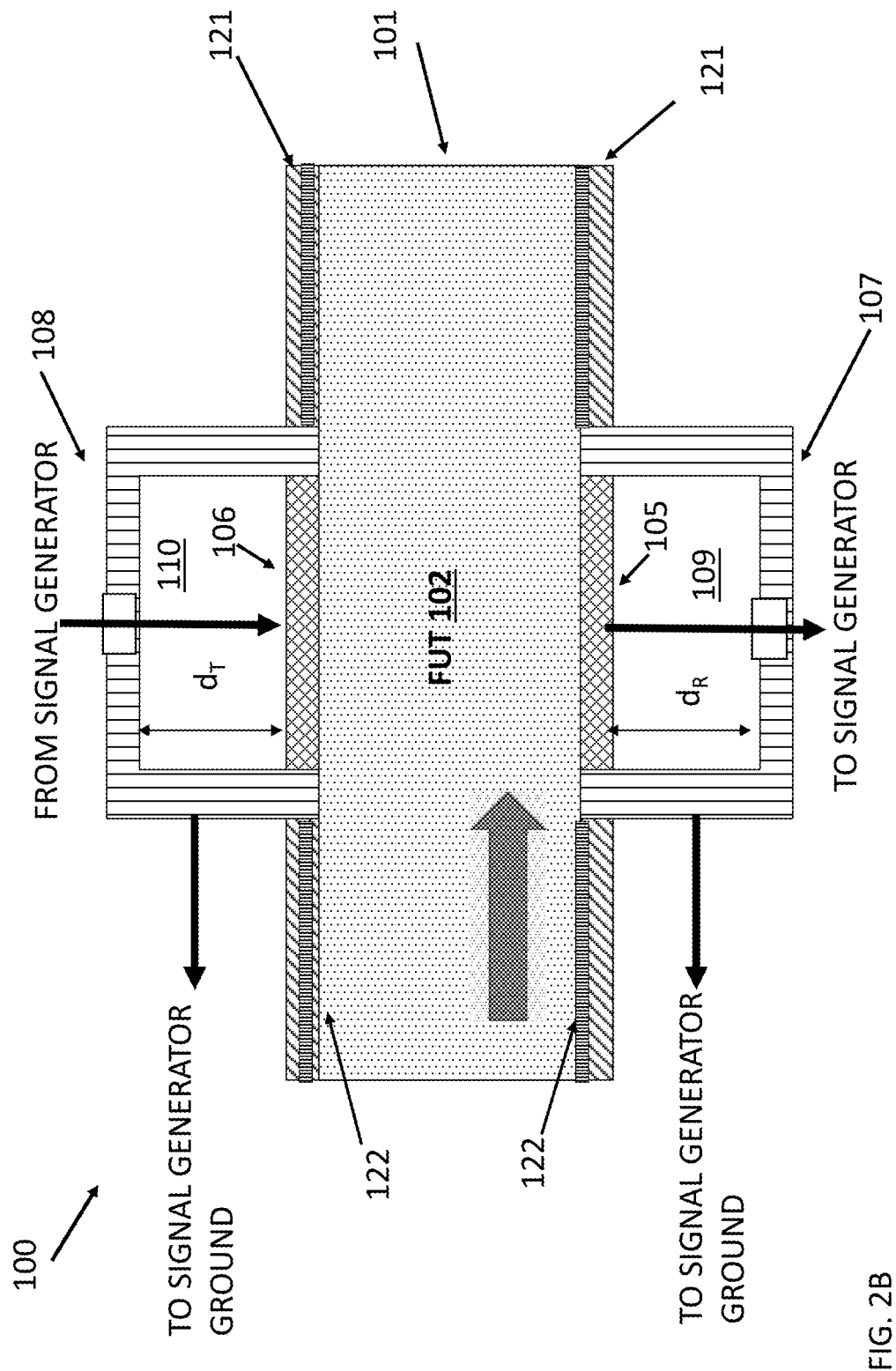
FIG. 2B is a sectional view of the sensor system in FIG. 1 according to various additional implementations.

FIGS. 2A and 2B present sectional views of sensor system 100 in sections AA delineated in FIG. 1. FIG. 2A illustrates one implementation of the system 100 with the fluid channel 101 defined by (electrically) non-conducting walls 125. FIG. 2B illustrates another implementation of the system 100 with the fluid channel 101 defined by walls 121 with non-conducting liners 122 disposed along an inner surface thereof. In some cases, the walls 121 shown in implementations in FIG. 2B are electrically conducting or electrically non-conducting. As described herein, the sensor system 100 includes transmitting electrode 105 with plate 107 which at least partially surrounds volume 109 proximate to the electrode 105, and a receiving electrode 106 with plate 108 which at least partially surrounds volume 110 proximate to the electrode 106. In particular implementations, the electrodes and conducting ground plates are circular in configuration and conform the interior circumference of the fluid channel 101. That is, in various implementations the electrodes 105 and 106 and corresponding portions of plates 107 and 108 have curved surfaces for conforming with the shape (arc) of the inner walls of the fluid channel 101. As also noted herein and can be seen in FIGS. 2A and 2B, the electrodes 105 and 106 are diametrically opposed across the fluid channel 101 and their centers are aligned with each other. As is evident in FIGS. 1, 2A and 2B, the inner surfaces of electrodes 105, 106 and corresponding plates 107 and 108 that are exposed to the fluid channel 101 are continuous with the inner surface of the fluid channel, e.g., forming a smooth surface along the fluid channel 101. As also noted herein, either of the electrodes 105 or 106 is selectable as the transmitting or receiving electrode(s). In particular implementation, if multiple transmitting or receiving electrodes are used (e.g., with three or more electrodes), all electrodes of the same type (transmitting/receiving) are located on the same side of the fluid channel 101.

While the description of sensor system 100 describes circular electrodes with a semi-cylindrical geometry to conform to the cylindrical fluid channel 101, the electrode geometry may be of any other shape such as rectangular, oval, etc. that can conform to the curved shape of the fluid channel 101.

Figure 3:
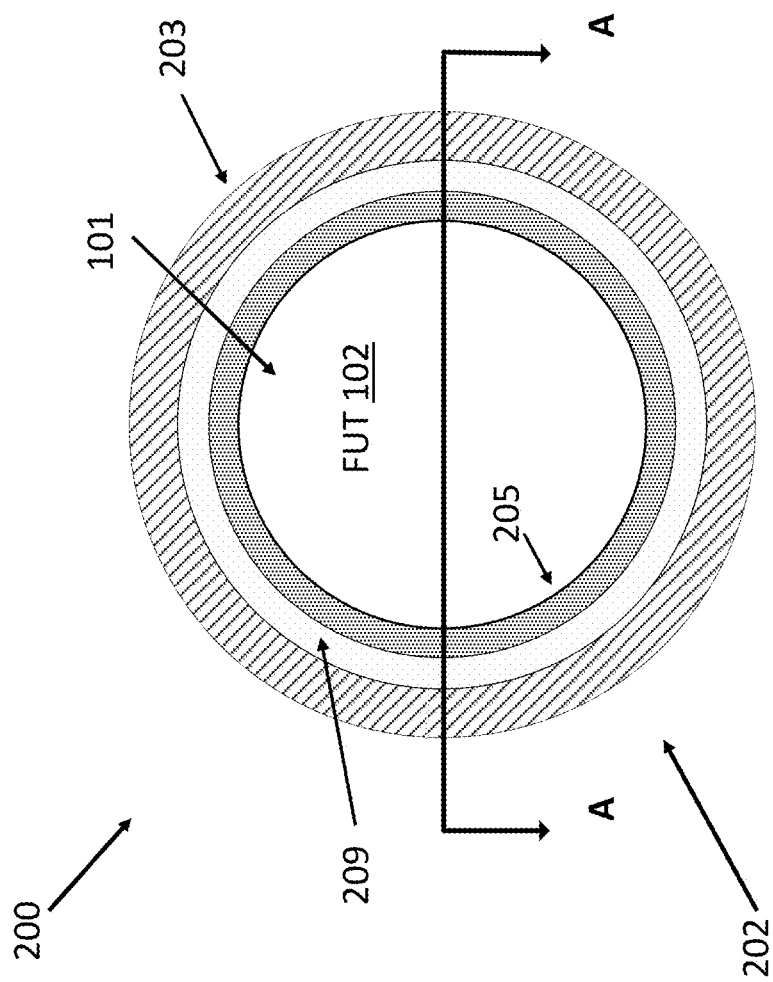
FIG. 3 is an end sectional view of a fluid channel and a portion of a sensor system according to various additional implementations.
Figure 4A:
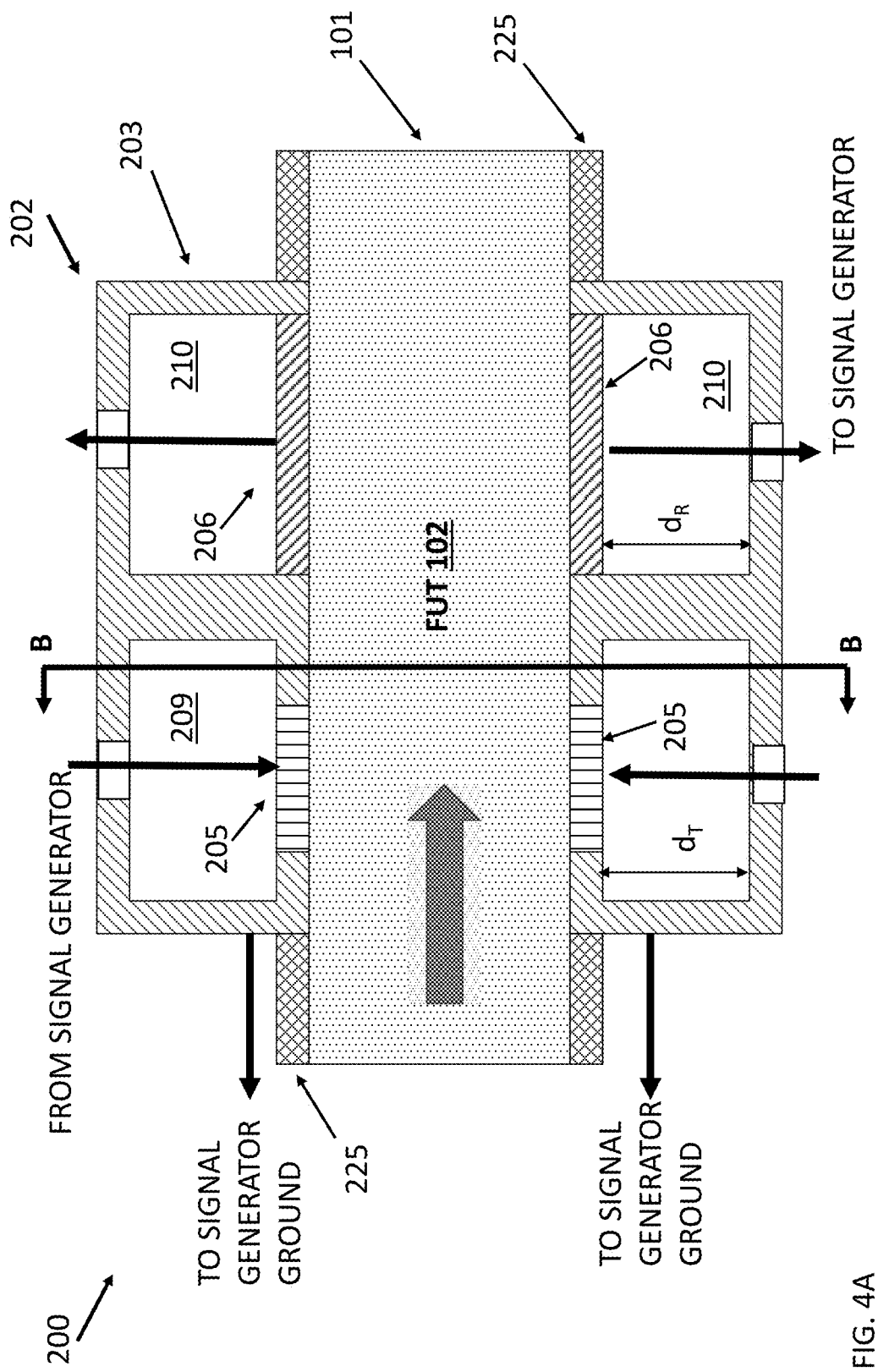
FIG. 4A is a longitudinal sectional view of the sensor system in FIG. 3 installed in a fluid channel, according to various implementations.
Figure 4B:
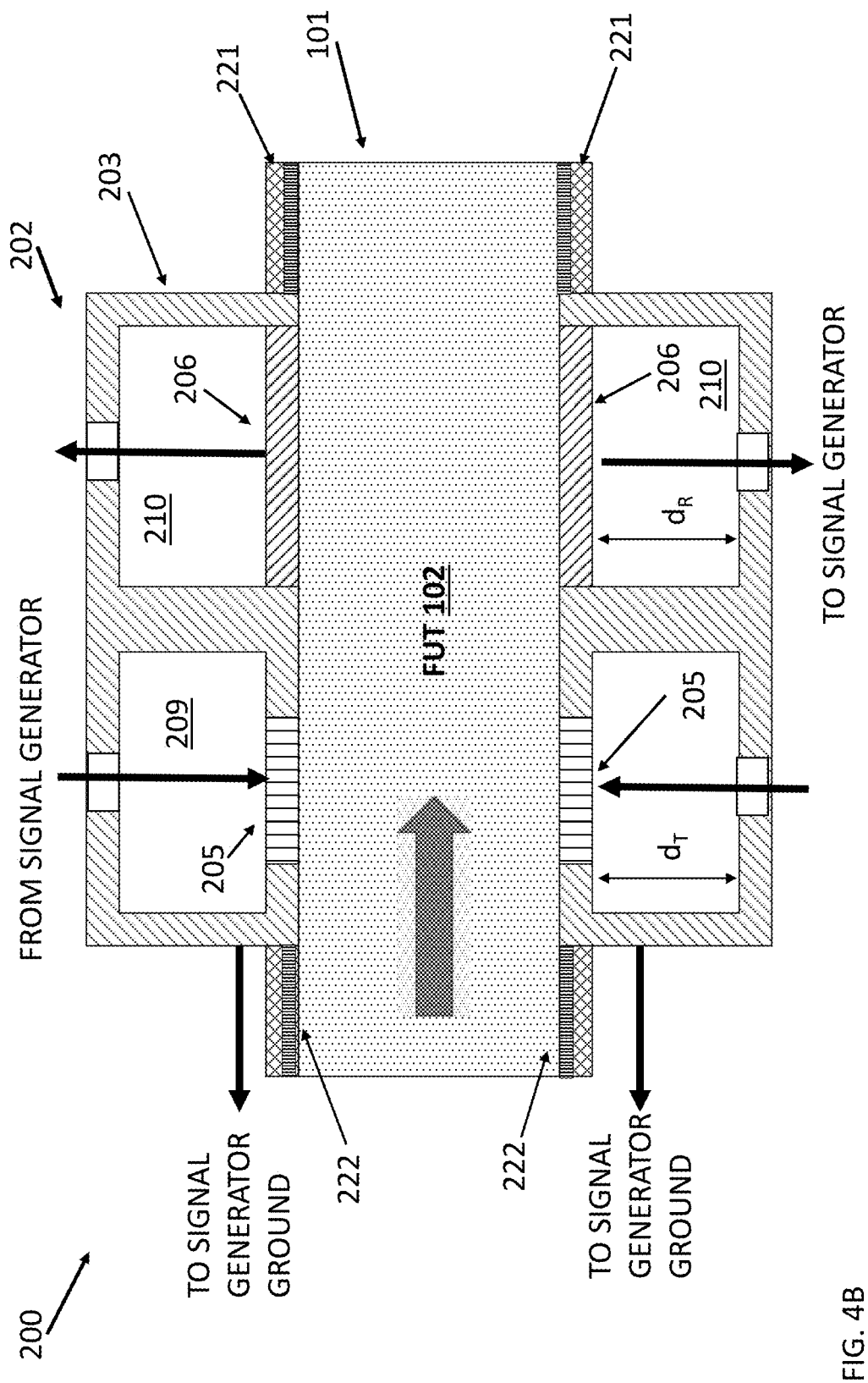
FIG. 4B is a longitudinal sectional view of the sensor system in FIG. 3 installed in a fluid channel, according to various additional implementations.

FIG. 3 is an end cross sectional view of a sensor system 200 according to various implementations. This view shows the sensor system 200 looking down a fluid channel 101. This view illustrates an electrode assembly 202 including a first cylindrical electrode 205 that extends circumferentially around the fluid channel 101, for example, having a cylindrical geometry conforming to the cylindrical fluid channel 101. Behind the electrode 205 is a backer ground plate (or simply, plate) 203 that encloses a capacitive volume 209. FIGS. 4A and 4B illustrate sectional views of the sensor system 200 taken through section AA.

Turning to FIG. 4A, one embodiment of system 200 is illustrated with non-conducting walls 225 surrounding (e.g., defining) the fluid channel 101. FIG. 4B illustrates an additional embodiment of system 200 with the fluid channel 101 defined by walls 221 that are at least partially lined with a non-conducting liner 222. The structural elements of the walls 221 may be electrically conducting or non-conducting. In particular implementations, sensor system 200 is comprised of two electrodes 205 and 206 which form portions of the interior circumferential surface of the fluid channel 201. In certain implementations, both electrodes 205, 206 are at least partially enclosed by the plate 203, defining both volumes 209 and 210 at least partially surrounding the back of electrodes 205, 206. That is, in various implementations, the plate 203 extends axially beyond the outer limits of the electrodes 205, 206 and in some cases, includes an interior wall that separates the electrodes 205, 206. As noted herein, in various embodiments, the electrodes 205, 206 and backer ground plate 203 have a cylindrical geometry conforming to the cylindrical fluid channel 101.

In sensor system 200, either electrode 205, 206 can act as a transmitting or receiving electrode. That is, relative to the illustrated left-to-right flow direction of the FUT 102, the first electrode 205 can be either a transmitting or receiving electrode, and the second electrode 206 can be an opposite electrode. In various implementations, if multiple sensor assemblies 202 are used, similar electrode types can be placed next to each other in line (e.g. transmitting next to transmitting, receiving next to receiving). The ground backer plate(s) 203 may take any number of forms, including those illustrated and described in U.S. patent application Ser. No. 62/619,275 (hereby incorporated by reference in its entirety), and can be adjustable to modify the distance of the electromagnetic field lines transmitted and received through the FUT 102 in the fluid channel 101. As described herein, the curved geometry of the electrodes 205, 206 will produce a complex three-dimensional field in addition to the interaction between the fields of the two sensor components.

According to various implementations, sensor systems 100 and 200 are located in a section of the cylindrical fluid channel 101 that is either constructed of a non-conducting material or lined with a non-conducting material. In various implementations, the conductive plates and electrodes must be electrically isolated from the container, or walls, defining the fluid channel 101. In certain implementations, the non-conducting portion 125 of the fluid channel 101 and/or the non-conducting liners 122 extend axially beyond the outer dimension of the plates (e.g., plates 107 and 108, or 203) at least two times the diameter of the fluid channel 101 on either side of the plates. This distance extends along the axis of the flow channel from the upstream and downstream edges of the backer ground plate 203. In various implementations, the plates (e.g., plates 107 and 108, or 203) of sensor systems 100 and 200 must be electrically insulated from any conductive elements of the fluid channel 101 as well as the electrodes 105, 106, and 205, 206.

Figure 5:
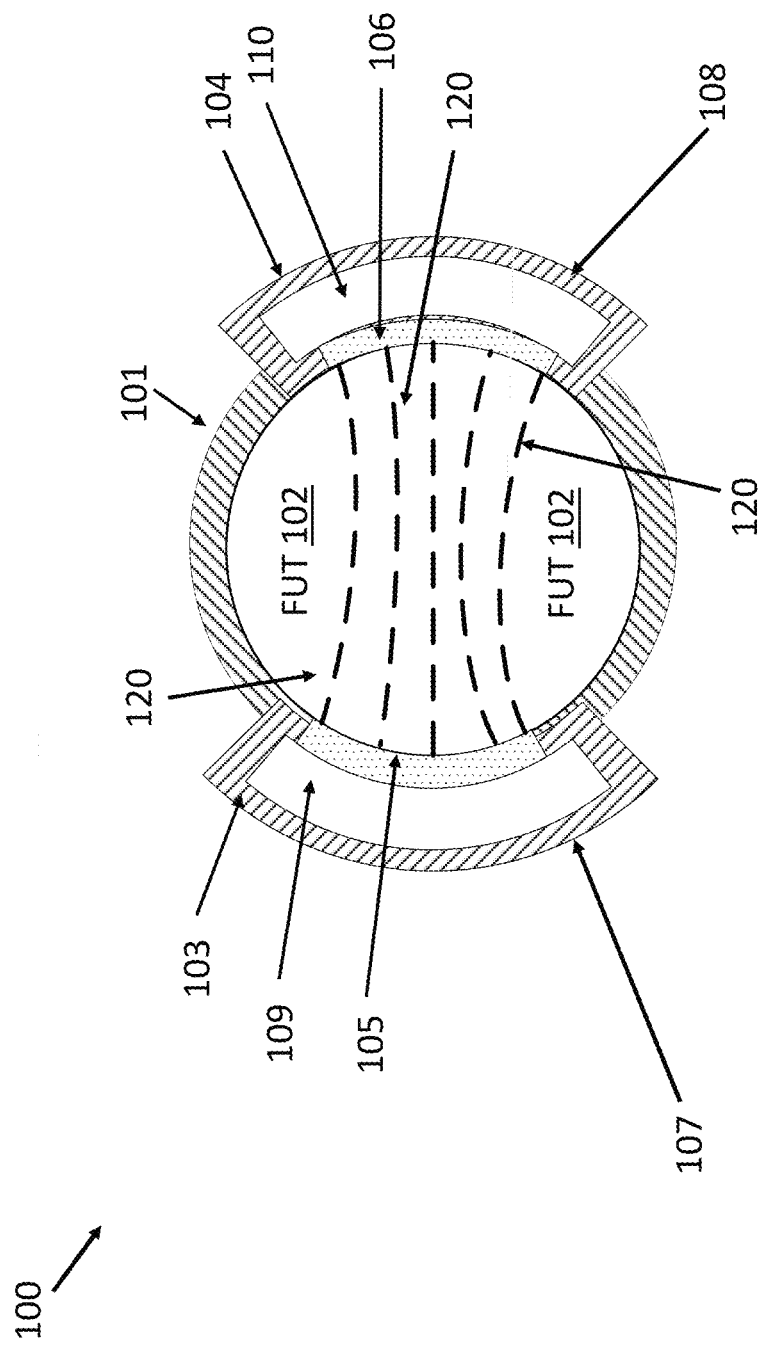
FIG. 5 illustrates example electromagnetic field lines generated by a system according to various implementations.

FIG. 5 illustrates an example configuration of the electromagnetic field lines 120 transmitted by sensor system 100 (FIG. 1) as they pass from the transmitting electrode 106 through the FUT 102 to the receiving electrode 105. This cross-sectional depiction illustrates the lines 120 through a plane perpendicular to the flow of FUT 102 in channel 101, and certain lines 120 through the center of the electrodes 105, 106. That is, in system 100, the electrodes 105, 106 transmit and receive signal (field lines 120) in the plane that sits across, or perpendicular, to the flow of the FUT 102 in channel 101. It is understood that the field lines 120 have a complex three-dimensional geometry reflecting the curved shape of the fluid channel 101 and the circular geometry of the electrodes 105, 106, and may vary from the simplified depiction in FIG. 5.

Figure 6:
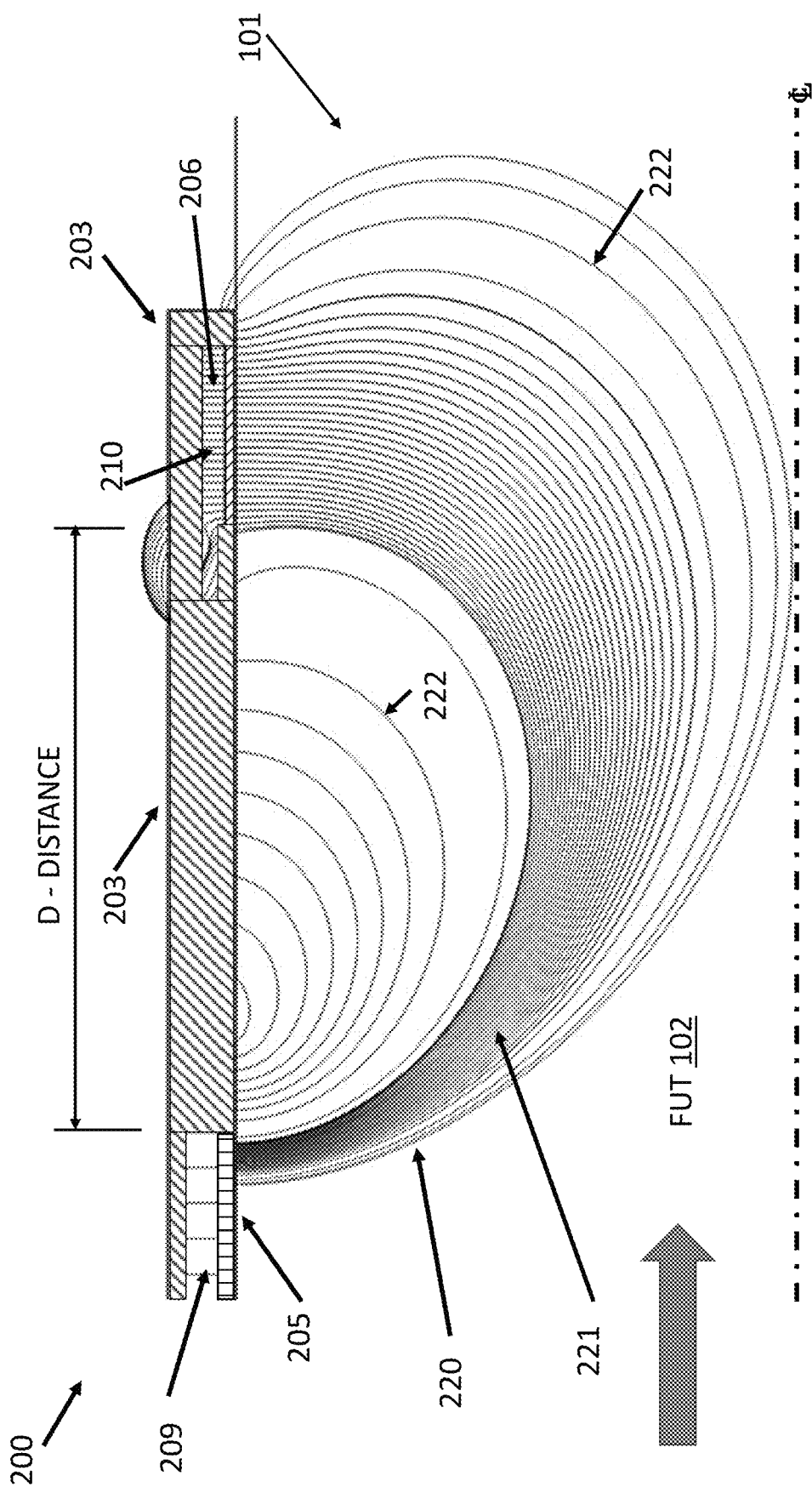
FIG. 6 illustrates example electromagnetic field lines generated by an additional system according to various implementations.

FIG. 6 illustrates an example configuration of the electromagnetic field lines 220 transmitted by sensor system 200 as they pass from the transmitting electrode 205 through the FUT 102 to the receiving electrode 206. This cross-sectional depiction illustrates the lines 220 through a plane parallel to the flow of the FUT 102 in the channel 101. That is, in system 200, the electrodes 205, 206 transmit and receive signal (field lines 220) in the plane that sits along, or parallel, to the flow of the FUT 102 in channel 101. In various implementations, field lines 220 travel only a portion of the width of the channel 101 (as measured from one side with electrodes 205, 206 to the opposite side). It is understood that the field lines 220 have a complex three-dimensional geometry reflecting the curved shape of the fluid channel 101 and the rectangular geometry of the electrodes 205, 206.

Referring to FIG. 6, not all field lines 220 actually measure the impedance characteristics of the FUT 102. In certain cases, only the field lines 221 that travel from the transmitting electrode 205 to the receiving electrode 206 measure characteristics of the FUT 102. Other field lines (e.g., field lines 222) travel from the transmitting electrode 205 to the conducting ground backer plate 203. These field lines 222 contribute to the parasitic capacitance in volumes 209 and 210 (and similarly in volumes 109 and 110 of sensor system 100 as discussed herein). The distance (e.g., width) of the transmission of the field lines 220 into the flow channel 101 is determined by the distance D between the transmitting electrode 205 and the receiving electrode 206. The value of D as defined by the spacing of the plate(s) 203 may be determined using the teachings of U.S. patent application Ser. No. 62/619,275 (previously incorporated by reference in its entirety), e.g., to adjust the distance (width) into the fluid channel 101 for the nominal penetration of the electromagnetic field, based on, among other things, the type of FUT.

With reference to both system 100 and system 200, the conductive backer ground plates 103, 104 (system 100) and 203 (system 200) around the transmitting electrodes (e.g., 106 in system 100 and 205 in system 200) and the receiving electrodes (e.g., 105 in system 100 and 206 in system 200) can be designed to help control the parasitic capacitances generated by the electric field lines (e.g., 120 in FIGS. 5 and 220 in FIG. 6) which traverse between the electrodes and the backer ground plates. Referring again to FIG. 6 it can be seen that some electromagnetic field lines (e.g., field lines 222) either traverse directly between the electrodes 205 and 206 to the plate 203 or pass through the FUT 102 to the plate 203. These fringing field lines that pass from electrodes 205 and 206 to plate 203 and the field lines that pass from electrode 205 through the FUT 102 to the plate 203 induce an electric potential in plate 203 which contributes to the parasitic capacitance of the volumes 209 and 210 between the electrodes 205 and 206 and plate 203. With reference to both system 100 and system 200, the capacitance volumes 109 and 110 in FIGS. 2A and 2B, and capacitive volumes 209 and 210 in FIGS. 4A and 4B are determined primarily by the distances between the electrodes and the plates, denoted as $d_T$ and $d_R$. Using a computational tool such as Comsol's Multiphysics, the distances between the transmitting electrodes and the plates noted as $d_T$ and between the receiving electrodes and the plates noted as $d_R$ can be designed to limit the effects of the parasitic capacitance on the impedance measurements.

The receiving electrodes (e.g., receiving electrode 105 in system 100 and receiving electrode 206 in system 200) and their corresponding backer ground plates (e.g., receiving electrode plate 103 and plate 203) act in a different manner. For example, the signal arriving at the receiving electrodes after passing through the FUT 102 varies with the material type (e.g., fluid characteristics and frequency). As the transmitted signal from transmitting electrodes passes through the FUT 102, the strength of the signal (magnitude) is attenuated, and the phase relation between the transmitted signal and the received signal is changed. As such, the potential of the signal and its phase relative to the transmitted signal is variable (e.g., by fluid type), and unknown a priori. The parasitic capacitance due to the field between the receiving electrodes and their backer ground plates have a larger effect on the measurement (when compared with the transmitting electrodes and their backer ground plates) due to the attenuation of the transmitted signals at the receiving electrodes. Therefore, the ability to reduce and control the parasitic capacitance for the receiving electrodes is significant to the quality of the data measured. Again, this may be achieved by the combination of controlling the potential of the backer ground plates (e.g., receiving electrode plate 103 and plate 203) and by designing the capacitive volumes behind receiving electrodes (e.g., capacitive volume 109 in system 100 and capacitive volume 210 in system 200) between the receiving electrodes and the conductive backer ground plates. Using a computational tool such as Comsol's Multiphysics, the distances between the receiving electrodes and the conducting ground plane plates noted as $d_R$ is designed to limit the effects of the parasitic capacitance on the impedance measurements.

The frequency range over which measurements of the impedance are made depends on the characteristics of the FUT 102 and, in general, typically range from approximately 1 KHz to approximately 100 MHz. Measurements can also be obtained at a specific single frequency within the typical range of selected frequencies. For example, where the FUT 102 includes dairy products, the frequency range can span around 1 KHz to around 1 MHz.

Figure 7:
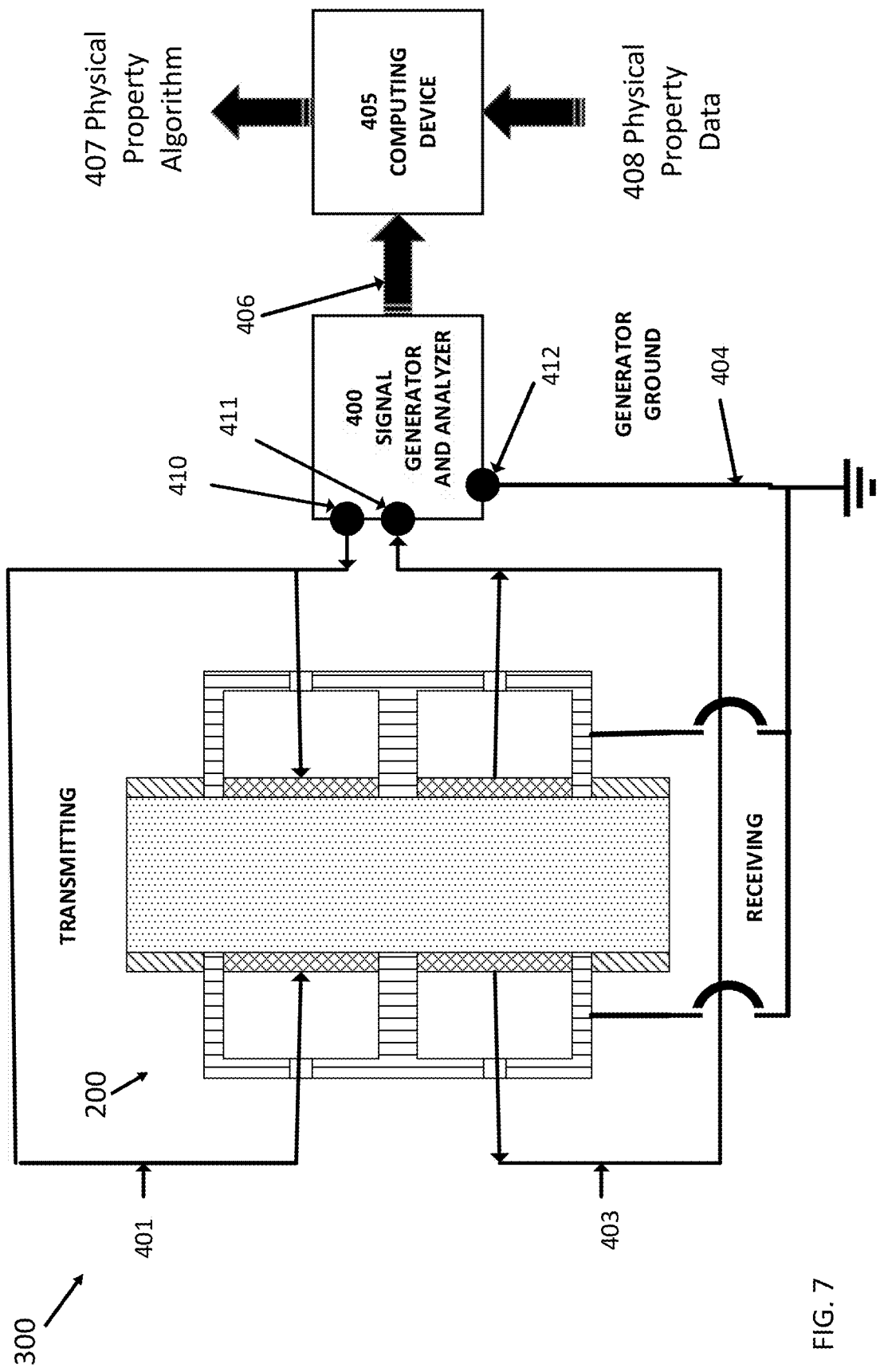
FIG. 7 shows a system including a signal generator/analyzer coupled with a sensor system according to various implementations.

FIG. 7 is a schematic depiction of a system 300 that includes the sensor system 200 coupled with a signal generator and analyzer 400, as well as a computing device 405. Additionally shown are connections between the signal generator and analyzer (or signal G/A) 400 and electrodes in sensor system 200. As noted herein, there are a number of devices known in the art that can be used to provide the function of a signal generator and/or signal analyzer, and in some cases, include separate components for performing one or more functions of the signal G/A 400. The signal G/A 400 is configured to generate and transmit signals through the FUT 102 via the electrodes (e.g., electrodes 205 and 206 in system 200). In various implementations, the computing device 405 is used to either correlate the spectrographic impedance or dielectric data 406 (provided by the analyzer portion of the signal G/A 400) with one or more physical properties of the FUT 102. In some cases, the computing device 405 correlates the spectrographic impedance or dielectric data 406 with at least one physical property using a correlation algorithm 407 or uses inputted physical property data 408 to develop the correlation algorithm 407.

While system 300 shown in FIG. 7 illustrates the connections between the electrodes and conducting ground backer plates of sensor system 200, the sensor system 200 can be substituted with sensor system 100 to work in conjunction with the other components in system 400. For example, the transmitting terminal 410 of the signal G/A 400 can be connected to the transmitting electrode(s) (e.g., transmitting electrode 106 in system 100 or transmitting electrode 205 in system 200) by a conductor 401. The receiving electrode(s) (e.g., receiving electrode 105 in system 100 and receiving electrode 206 in system 200) are connected by conductor 403 to the receiving terminal 411 of the signal G/A 400. The plates (e.g., plates 103, 104, or plate 203) are connected to the ground terminal 412 of the signal G/A 400.

Figure 8:
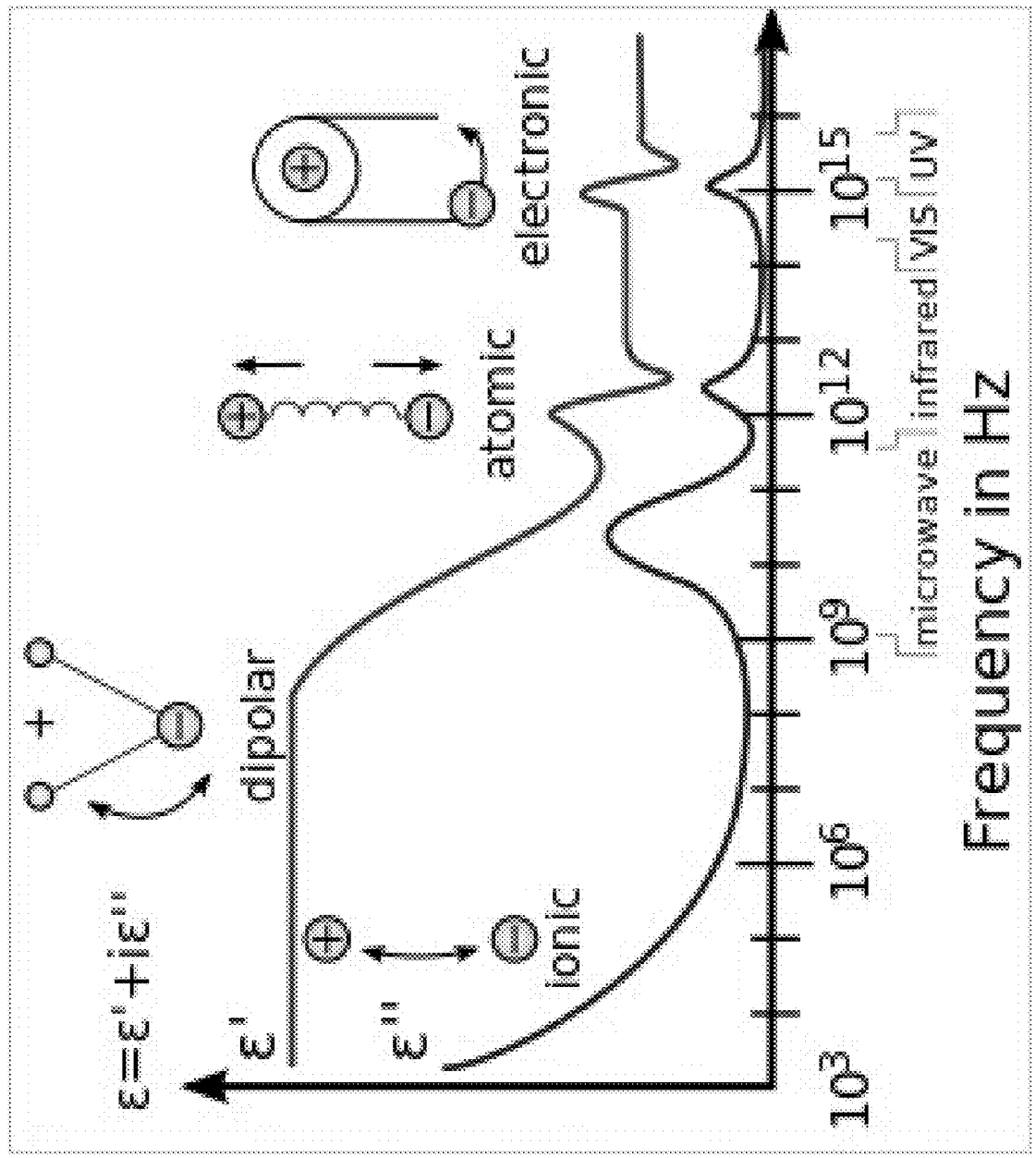
FIG. 8 illustrates impedance characteristics of water with varying frequency according to Reference 7.
Figure 9:
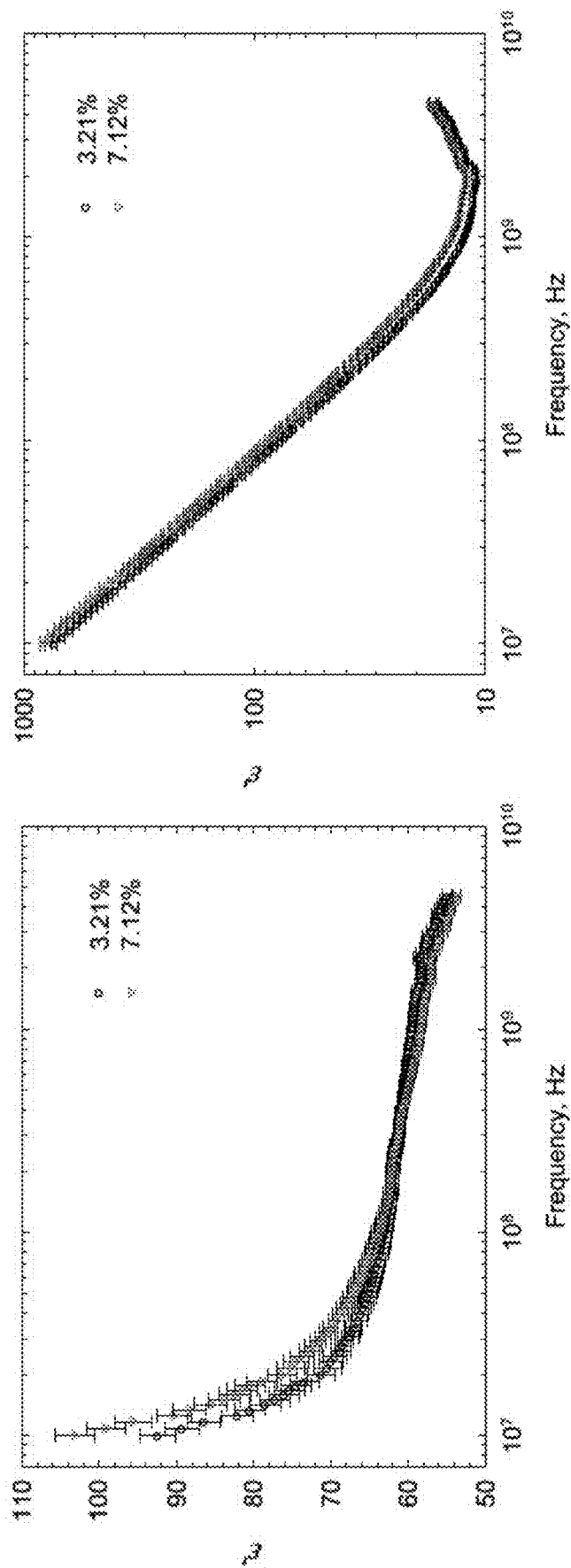
FIG. 9 illustrates impedance characteristics of milk with varying frequency with different levels protein content according Reference 3.
Figure 10:
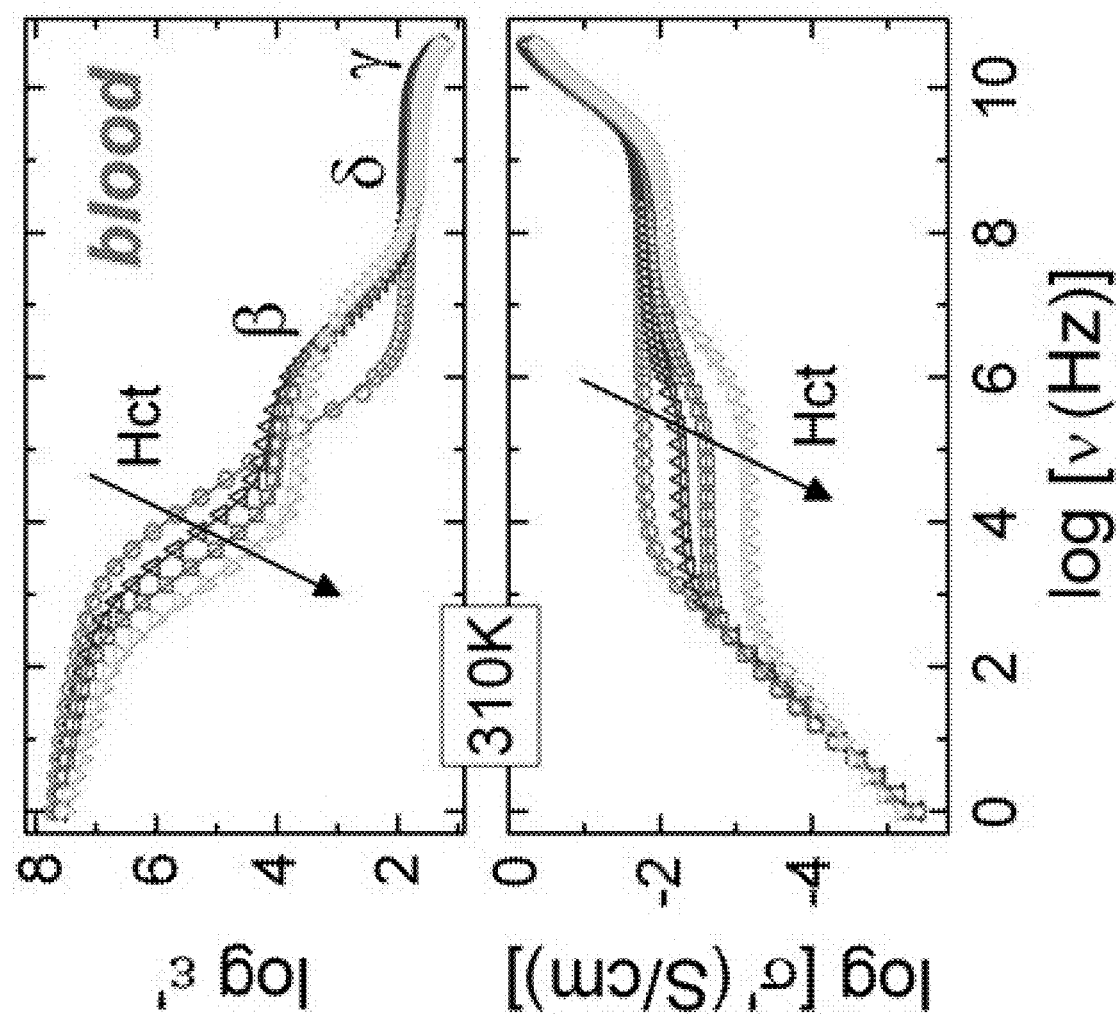
FIG. 10 illustrates impedance characteristics of human blood with varying frequency according to Reference 8.

FIGS. 8, 9, and 10 present information on the observed variations in the spectrographic impedance of an inorganic fluid (e.g., water, FIG. 8, described in Reference 7), an organic fluid (e.g., milk, FIG. 9 described in Reference 3), and a biological fluid (e.g., blood, FIG. 10, described in Reference 8). By using precise values of impedance or dielectric over a range of frequencies specific to the FUT of interest, and applying one or more of the various approaches known in the art (e.g. ANOVA or deep learning) to make correlations between the spectrographic impedance or dielectric and desired physical property(ies) of the FUT, an algorithm may be developed to provide a measure of the desired physical property(ies) during an in-process monitoring of the FUT.

REFERENCES

The following References are each incorporated herein by reference in its entirety:
1) Bertemes-Filho, P., et al; "Bioelectrical Impedance Analysis for Bovine Milk: Preliminary Results" Journal of Physics: Conference Series Vol 224 No. 1, 2010;
2) Grossi, M., et al: "Fast and Accurate Determination of Olive Oil Acidity by Electrochemical Impedance Spectroscopy" IEEE Sensors Journal 2014, 14 (9) pp. 2947-2954;
3) Zhu, Z., et al; "Dielectric Properties of Raw Milk as Functions of Protein Content and Temperature" Food Bioprocess Technology (2015) 8:670-680;
4) Das, S., et al; "Milk Adulteration and Detection: A Review" Sensor Letters Vol 14, 1-18 2016;
5) Ziatev, T. and Vasilev, M.: "Contactless Methods for Quality Evaluation of Dairy Products" Applied Research in Technics, Technologies, and Education Vol. 4, No. 1, 2016;
6) Grossi, M. and Ricco, B.; "Electrical Impedance Spectroscopy (EIS) for Biological Analysis and Food Characterization: A Review" Journal of Sensors and Sensor Systems Vol. 6 pp. 303-325, 2017;
7) Wikipedia https://en.wikipedia.org/wiki/Dielectric spectroscopy attributed to Dr. Kenneth Mauritz; and
8) Wolf, M., et al; "Broadband Dielectric Spectroscopy on Human Blood" Biochinica et Biophysica Acta Vol 1810, No. 8 Aug. 2011 PP 727-740.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random-access memory or both. Components of a computer include a processor for executing instructions and one or more memory devices for storing instructions and data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:
1. A system for measuring an electromagnetic impedance characteristic of a fluid under test (FUT) in a fluid channel, the system comprising:

a transmitting electrode assembly comprising:
  a transmitting electrode having a transmitting surface; and
  a transmitting electrode backer ground plate at least partially surrounding the transmitting electrode;
a receiving electrode assembly comprising:
  a receiving electrode having a receiving surface; and
  a receiving electrode backer ground plate at least partially surrounding the receiving electrode;
wherein the transmitting electrode and the receiving electrode are located in a set of walls defining the fluid channel, the transmitting surface and the receiving surface each conform to a shape of the set of walls defining the fluid channel, wherein the fluid channel permits transverse flow of the FUT relative to both the transmitting electrode and the receiving electrode,
wherein the transmitting electrode backer ground plate extends from a plane formed by the transmitting electrode and creates an electrically isolated volume behind the transmitting electrode, and wherein the receiving electrode backer ground plate extends from a plane formed by the receiving electrode and creates an electrically isolated volume behind the receiving electrode,
wherein during use, the electrically isolated volume behind the transmitting electrode and the electrically isolated volume behind the receiving electrode aid in controlling parasitic capacitances generated by an electromagnetic field including field lines extending between the transmitting electrode and the receiving electrode.

2. The system of claim 1, wherein the transmitting electrode is substantially parallel with the receiving electrode, and wherein a center of the transmitting electrode is aligned with a center of the receiving electrode across the fluid channel.

3. The system of claim 1, wherein the transmitting electrode backer ground plate is electrically grounded and insulated from the transmitting electrode;
  wherein the receiving electrode backer ground plate is electrically grounded and insulated from the receiving electrode; and
  wherein the transmitting electrode backer ground plate has a surface that is coplanar with the transmitting electrode in the fluid channel, and wherein the receiving electrode backer ground plate has a surface that is coplanar with the receiving electrode in the fluid channel.

4. The system of claim 1, wherein the transmitting electrode conductive backer ground plate and the receiving electrode conductive backer ground plate are each circular, and wherein a diameter of the transmitting electrode is equal to approximately a diameter of the receiving electrode.

5. The system of claim 1, wherein the set of walls includes a pair of openings including an inlet and an outlet, wherein the FUT flows from the inlet to the outlet, and wherein the transmitting electrode assembly and the receiving electrode assembly are located between the openings.

6. The system of claim 1, wherein the transmitting electrode and the receiving electrode are defined by rings with a cylindrical geometry conforming to the inner surface of the set of walls.

7. The system of claim 1, wherein the transmitting electrode conductive backer ground plate and the receiving electrode conductive backer ground plate are integral with the set of walls defining the fluid channel, wherein the transmitting electrode conductive backer ground plate and the receiving electrode conductive backer ground plate conform to a geometry of the set of walls defining the fluid channel.

8. The system of claim 1, wherein the transmitting electrode and the receiving electrode are axially adjacent one another in the fluid channel,
  wherein the system further comprises:
    an additional transmitting electrode assembly with an additional transmitting electrode and an additional receiving electrode assembly with an additional receiving electrode, located axially adjacent one another and diametrically opposing the transmitting electrode assembly and the receiving electrode assembly,
    wherein during use, electromagnetic signals between the transmitting electrode and the receiving electrode and the additional transmitting electrode and the additional receiving electrode form an arc that spans at least partially axially along the fluid channel,
    wherein the transmitting electrode is located upstream of the receiving electrode or the receiving electrode is located upstream of the transmitting electrode.

9. The system of claim 1, wherein the FUT comprises a liquid, a gas, or an organic fluid comprising milk,
  wherein each electrically isolated volume is defined by a distance ($d_T$ and $d_R$) between a back of the transmitting electrode and the transmitting backer ground plate, and a back of the receiving electrode and the receiving backer ground plate, respectively, wherein during use, parasitic capacitances in the electrically isolated volumes are at least partially controlled by the distances ($d_T$ and $d_R$).

10. The system of claim 1, wherein the transmitting electrode and the receiving electrode are in electrically conducting contact with the FUT.

11. The system of claim 1, wherein the transmitting electrode and the receiving electrode are in non-electrical conducting contact with the FUT.

12. The system of claim 1, wherein the transmitting electrode assembly comprises at least one additional transmitting electrode and wherein the receiving electrode assembly comprises at least one additional receiving electrode,
  wherein respective electrodes in the transmitting electrode assembly are configured to operate at a single frequency or at distinct frequencies within a range of selected frequencies, and
  wherein respective electrodes in the receiving electrode assembly are configured to operate at the single frequency or at the distinct frequencies within the range of selected frequencies,
  wherein adjacent electrodes in each of the transmitting electrode assembly and the receiving electrode assembly have a same function.

13. The system of claim 1, further comprising a signal generator/analyzer coupled with the transmitting electrode and the receiving electrode, the signal generator/analyzer comprising:
  a generator component configured to initiate transmission of a set of electromagnetic signals from the transmitting electrode, through the FUT, to the receiving electrode; and
  an analyzer component configured to detect a change in the set of electromagnetic signals from the transmitting electrode to the receiving electrode,
  wherein the set of electromagnetic signals are transmitted over a frequency range of approximately 1 kilo-Hertz to approximately 100 mega-Hertz.

14. The system of claim 13, further comprising a computing device coupled with the signal generator/analyzer, wherein the computing device is configured to determine a characteristic of the FUT based upon a change in the set of electromagnetic signals from the transmitting electrode to the receiving electrode,
  wherein each electrically isolated volume is defined by a distance ($d_T$ and $d_R$) between a back of the transmitting electrode and the transmitting backer ground plate, and a back of the receiving electrode and the receiving backer ground plate, respectively, wherein during use, parasitic capacitances in the electrically isolated volumes are at least partially controlled by the distances ($d_T$ and $d_R$).

15. The system of claim 13, wherein determining the characteristic of the FUT comprises:
  determining a difference in an aspect of the set of electromagnetic signals;
  comparing the difference in the aspect to a predetermined threshold; and
  determining a characteristic of the FUT based on the compared difference.

16. The system of claim 15, wherein determining the characteristic of the FUT comprises:
  computing impedance or dielectric characteristics of the FUT; and
  applying an established correlation algorithm to the computed impedance or dielectric characteristics to determine the characteristic of the FUT.

17. The system of claim 13, wherein a size of the electromagnetic field is fixed based upon a geometry of the sensor system, a diameter of the fluid channel, and electromagnetic properties of the FUT,
  wherein each electrically isolated volume is defined by a distance ($d_T$ and $d_R$) between a back of the transmitting electrode and the transmitting backer ground plate, and a back of the receiving electrode and the receiving backer ground plate, respectively,
  wherein during use, parasitic capacitances in the electrically isolated volumes are at least partially controlled by the distances ($d_T$ and $d_R$).

18. A method of measuring an electromagnetic impedance characteristic of a fluid under test (FUT) in a fluid channel, the method comprising:
  providing a system comprising:
    a transmitting electrode assembly comprising:
      a transmitting electrode having a transmitting surface; and
      a transmitting electrode backer ground plate at least partially surrounding the transmitting electrode;
    a receiving electrode assembly comprising:
      a receiving electrode having receiving surface; and
      a receiving electrode backer ground plate at least partially surrounding the receiving electrode,
    wherein the transmitting electrode and the receiving electrode are located in a set of walls defining the fluid channel, the transmitting surface and the receiving surface each conform to a shape of the set of walls defining the fluid channel,
    wherein the transmitting electrode backer ground plate extends from a plane formed by the transmitting electrode and creates an electrically isolated volume behind the transmitting electrode, and wherein the receiving electrode backer ground plate extends from a plane formed by the receiving electrode and creates an electrically isolated volume behind the receiving electrode;
  flowing the FUT through the fluid channel;
    transmitting a set of electromagnetic signals from the transmitting electrode, through the FUT, to the receiving electrode while flowing the FUT through the fluid channel; and
    detecting a change in the set of electromagnetic signals from the transmitting electrode to the receiving electrode,
    wherein during use, the electrically isolated volume behind the transmitting electrode and the electrically isolated volume behind the receiving electrode aid in controlling parasitic capacitances generated by an electromagnetic field including field lines extending between the transmitting electrode and the receiving electrode.

19. The method of claim 18, wherein the set of electromagnetic signals are transmitted over a predefined frequency range between approximately 1 kilo-Hertz to approximately 100 mega-Hertz,
  wherein the set of electromagnetic signals define the electromagnetic field including the field lines extending from the transmitting electrode, through the FUT, to the receiving electrode through, and wherein a size of the electromagnetic field is fixed based upon a geometry of the sensor system, a diameter of the fluid channel, and electromagnetic properties of the FUT.

20. The method of claim 18, further comprising determining a characteristic of the FUT based upon a change in the set of electromagnetic signals from the transmitting electrode to the receiving electrode, wherein determining the characteristic of the FUT comprises:
  determining a difference in an aspect of the set of electromagnetic signals;
  comparing the difference in the aspect to a predetermined threshold; and
  determining a characteristic of the FUT based on the compared difference, wherein determining the characteristic of the FUT comprises:
    computing impedance or dielectric characteristics of the FUT; and
    applying an established correlation algorithm to the computed impedance or dielectric characteristics to determine the characteristic of the FUT.

\* \* \* \* \*